(12) United States Patent
Durig et al.

(10) Patent No.: US 6,592,901 B2
(45) Date of Patent: Jul. 15, 2003

(54) HIGHLY COMPRESSIBLE ETHYLCELLULOSE FOR TABLETING

(75) Inventors: Thomas Durig, Malvern, PA (US); Ronald Haywood Hall, Richmond, VA (US); Richard A. Salzstein, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 10 days.

(21) Appl. No.: 09/977,785

(22) Filed: Oct. 15, 2001

(65) Prior Publication Data

US 2003/0077327 A1 Apr. 24, 2003

(51) Int. Cl.⁷ ............................. A61K 9/14; A61K 9/20
(52) U.S. Cl. ...................... 424/489; 424/406; 424/464; 424/465; 424/480

(58) Field of Search ................................ 424/480, 495, 424/489, 464, 465

(56) References Cited

U.S. PATENT DOCUMENTS 3,870,790 A * 3/1975 Lowey et al. .................. 424/19
5,082,669 A * 1/1992 Shirai et al. ................ 424/495

* cited by examiner

*Primary Examiner*—Thurman K. Page
*Assistant Examiner*—Micah-Paul Young
(74) *Attorney, Agent, or Firm*—David Edwards

(57) ABSTRACT

A pharmaceutical dosage form composition is composed of an ethylcellulose that has an ethoxyl range lower limit of 49.6%, an a viscosity of less than 53 cps and at least one active pharmaceutical ingredient. This dosage form is highly compressible and compactible forming harder tables or pellets with better release retardation than comparable prior art tablets.

17 Claims, No Drawings

HIGHLY COMPRESSIBLE ETHYLCELLULOSE FOR TABLETING

FIELD OF INVENTION

The present invention relates to the use of a type of ethylcellulose that is highly compressible and compactible in the manufacture of pharmaceutical solid dosage forms.

BACKGROUND

Ethylcellulose (EC) is frequently used in the pharmaceutical industry as an excipient to provide a diffusion barrier function, thus limiting the diffusion of aqueous fluids into a system and limiting diffusion of dissolved actives out of the system. This functionality can be utilized in areas such as controlled release, stabilizing film coatings, and taste masking. Additionally, EC is utilized as a binder in compressed tablet systems where the high plasticity of EC contributes to the cohesion and mechanical strength of the tablet compact.

In order to incorporate EC into a product, a number of different processes can be used. Organic solvent-based processes are frequently utilized for film coating and microencapsulation (Morse et al, U.S. Pat. No. 3,860,733 (1972); Kent, D. J. and Rowe, R. C., "Solubility Studies on Ethylcellulose used in Film Coating", J. Pharm. Pharmacol., Vol. 31, 1978, pp. 808–819). Alternately, EC can be dispersed in aqueous based latex systems for film coating. EC may also be thermally processed, as in melt extrusion or injection molding. Lastly, direct compression and wet granulation tablet manufacturing processes that produce either monolithic or multi-layer systems have been exploited in the pharmaceutical arena (Dahlinder, L. E., Graffner, C., and Sjoregen, "Strength of the Insoluble Residues of Plastic Matrix Slow Release Tables (Duretter) In Vitro and In Vivo", Acta Pharm. Suec., Vol. 10, 1973, pp. 323–332; and Shlieout, G. and Zessin, G., "Investigation of Ethylcellulose as a Matrix Former and a New Method to Regard and Evaluate the Compaction Data", Drug Development Ind., Vol. 22, No. 4, 1996, pp. 313–319; Colombo, P. et al, "System for the Controlled-rate Release of Active Substances", European Patent 0 226 884 B1, 1990.)

Tablets based on inert plastic deforming polymers such as EC (also referred to as "inert plastic matrix tablets") were first introduced in 1960 and have found extensive clinical application (Chang, R. K. and Robinson, J. R., Sustained Drug Release from Tablets and Particiles through Coating in "Pharmaceutical Dosage forms: Tablets", (Lieberman, H. A., Lachman, L. and Schwartz, J. B. Eds.), $2^{nd}$ Ed., Marcel Dekker, New York, N.Y., 1990, pp. 239–241). In particular in the area of direct compression, a number of reports have been published describing the use of EC in directly compressed tablet systems. Upadrashta, S. M., Katikaneni, P. R., Hileman, G. A. and Keshary, P. R., (in "Direct Compression Controlled Release Tablets using Ethylcellulose Matrices", Drug Dev. Ind. Pharm. Vol. 19, 1993, pp. 449–460) report a systematic study of the effect of different types of EC (N-type, 48.0–49.5% ethoxyl content) on directly compressed matrix tablets in combination with varying proportions of theophylline or indomethacin to make controlled release matrix tablets. They observed that EC of low (10 cps) viscosity (low viscosity corresponds to low molecular weight) resulted in harder tablets than when high 100 cps) viscosity EC was used and compressed at the same pressure. Furthermore, the greater mechanical strength was correlated with greater drug release retardation. Upradashta, S. M., Katikaneni, P. R., Hileman, G. A., Neau, S. H. and Rowlings, C. E., (in "Compressibility and Compactibility Properties of Ethylcellulose, Int. J. Pharm. Vol. 112, 1994, pp. 173–179) further reported on the compressibility and compactibility of N-type (48.0–49.5% ethoxyl content) EC. Based on hardness-compression force profiles, Heckel plots, and force-displacement profiles, Upradashta et al. again concluded that lower viscosity (lower molecular weight) EC yields harder tablets. Furthermore, lower molecular weight was correlated with lower mean yield pressures, indicating greater plasticity, while higher molecular weight EC was associated with an increase in elastic work. Shliehout and Zessin (ibid) who studied EC (48.0–49.5% ethoxyl content) independently confirmed these findings with EC of 7, 22 and 100 cps viscosities.

Katikaneni, P. R., Upadrashta, S. M., Rowlings, C. E., Neau, S. H. and Hileman, G. A., (in "Consolidation of Ethylcellulose: Effect of Particle Size, Press Speed and Lubricants, Int. J. Pharm., Vol. 117, 1995, pp. 13–21) further reported on the effect of particle size and press speed on the consolidation of the above mentioned EC N-types. As particle size was decreased from 420–840 $\mu$m to 105–149 $\mu$m, the tablet hardness was markedly increased. Simultaneously, mean yield pressure was found to decrease with decreased particle size. Conversely, the elastic work increased with the use of larger particle size EC.

In an attempt to advance the utility of EC in direct compression and particularly for controlled release dosage forms, micronized ethylcellulose (48.0–49.5% ethoxyl content, 7–41 $\mu$m average particle size) has been proposed as a directly compressible matrix former by Pollock, D. K. and Sheskey, P. J., (in "Micronized Ethylcellulose: Opportunities in Direct Compression Controlled Release Tablets", Pharm. Tech., Vol. 20 (9), 1996, pp. 120–130). These authors compared various viscosity types (7, 10, and 100 cps). Furthermore, a comparison was made with analogous ethylcellulose in granular form (average particle size 310–465 $\mu$m). Diphenhydramine was used as a water-soluble model drug. Their findings were that higher EC concentration and smaller EC particle size led to a marked reduction in EC drug release rates. Furthermore, they found that micronized EC achieved greater tablet hardness than granular EC when the same compression force was used. This greater tablet hardness was again observed to lead to lower release rates (greater prolongation of release duration). A further finding was that the drug release rate was lower from tablets containing micronized EC when compared to tablets containing granular EC, where the two types of tablets were compressed to the same hardness. Apparently, these differences in tablet properties were caused by the differences between the particle sizes of the drug and the two types of EC studied.

However, in the above study as well as in other studies where micronized EC has been used, tablets were prepared manually, "one at a time", using a hydraulic laboratory press. A key requirement for large-scale commercial tablet manufacturing using an automated rotary press is that the powders that are to be compressed should have fast and relatively unimpeded and uniform flow under gravity. Without this prerequisite, powder flow from the hopper of a tablet press into the tablet feedframe and then into the die cavities will not be fast and uniform enough to ensure uniform and reliable tablet weight and hardness. Furthermore, uniform flow is needed to avoid damage to the tooling due to insufficient filling of the die cavities resulting in contact between the upper and lower punches (Banker, G. S. and Anderson, N. R., Tablets in "The Theory and Practice of Industrial Pharmacy" (Lachman, L., Lieberman, H. A. and Kanig, J. L., Eds.), Edition, Lea and Febiger, Philadelphia, Pa., 1986, pp. 293–345). Particle size is one of the key parameters affecting powder flow. It is generally accepted that as particle size decreases, powder flowability improves with the optimum occurring in the size range of about 100–400 μm (Fassihi, A. R. and Kanfer, I., "Effect of Compressibility and Powder Flow Properties on Tablet Weight Variation", Drug Development Ind. Pharm., Vol. 12, 1986, pp. 1947–1958). Below this level, decreased particle size can lead to rapid increase in inter-particle interaction resulting in an increase in cohesive forces (Randall, C. S., Particle Size Distribution in "Physical Characterization of Pharmaceutical Solids", (Brittain, H. G., Ed.), Marcel Dekker Inc., New York, 1995, pp. 180–182). Due to its fine nature, micronized EC (particle size 7–41 μm) is a cohesive powder, which is generally prone to poor powder flow (as will be shown in Table 1 below).

There are also powder handling concerns with fine, micronized pharmaceutical powders. In addition to the large surface area, these powders tend to have low bulk densities, thus predisposing them to become airborne, which leads to greater dust formation during compaction. The low bulk density of an excipient also reduces the maximum fill weight that can be achieved on a rotary press (as will be shown in Example 2). High dustiness not only poses potential occupational safety and contamination hazards, but also results in decreased efficiency and uncertain weight as a portion of the material to be compressed for each tablet becomes airborne.

Examples of prior art that uses dry solid material including ethylcellulose with compression for producing sustained release tablets are U.S. Pat. No. 3,632,739, PCT/WO 00/19985, PCT/WO 99/06045, and EP 0 875 245 A2.

A need, therefore, exists for a directly compressible form of EC with high compressibility and compactibility, thus allowing the formation of harder tablets, and potentially better release retardation, while providing excellent powder flow and low dusting, in order to facilitate its use in commercial scale high-speed tablet manufacturing.

SUMMARY OF THE INVENTION

This invention is directed to a pharmaceutical composition that uses a form of ethylcellulose that provides for high compressibility and compactibility of the composition, without the need for post-synthesis micronization of the EC and with excellent flow characteristics but low dusting; this EC allows compressed dosage forms to have superior mechanical strength.

The present invention is directed to a pharmaceutical dosage form comprising a) ethylcellulose that has an ethoxyl range lower limit of 49.6% and a viscosity of less than 53 cps using a Hercules Horizontal Capillary Viscometer (following ASTM Method D914-00) at a temperature of 25° C. in a 5% solution and b) at least one active pharmaceutical ingredient.

DETAILED DESCRIPTION OF THE INVENTION

In accordance with the present invention, it has been surprisingly found that compression of highly substituted (49.6–54.88% ethoxyl content), low viscosity (less than 53 cps) EC yields tablets of superior mechanical strength when compared to the analogous dosage form prepared with EC of lower ethoxyl content and/or higher viscosity. Furthermore, this form of EC has been found to yield compressed tablets that surpass the mechanical strength of comparable tablets using commercially available pharmaceutical grades of micronized EC. Furthermore, this form of EC is found to possess good powder flow and low dusting.

Ethylcellulose is a cellulose ether that is versatile with many uses. The following grade types of EC are commercially available from Hercules Incorporated:

| Type | Ethoxy Content (%) | Degree of Substitution (DS) |
|---|---|---|
| K | 45.0–47.3 | 2.22–2.41 |
| N | 48.0–49.5 | 2.46–2.58 |
| T | 49.6–51.5 | 2.58–2.73 |
| X | 50.5–52.5 | 2.65–2.81 |

Types K, N, and T of EC are used in food and food contact applications. More specifically, K and T are used for food and contact such as paper or paperboard in contact with food. Prior to this invention, N types were used as a binder or coating in pharmaceutical applications. Type X is used in inks and other industrial applications.

It is well known in the art how to make EC. Normally, either chemical grade cotton linters or wood pulp is used to prepare EC. The sequence of chemical reactions is similar to that for methylation of cellulose. In commercial practice, sodium hydroxide concentrations of 50% or higher are used to prepare the alkali cellulose. Staged additions of solid sodium hydroxide during the reactions can be used to reduce side reactions. Ethyl chloride is added to the alkali cellulose in nickel-clad reactors at 90–150° C. and 828 to 965 kPa (120 to 140 psi) for 6–12 hours. Diluents such as benzene or toluene can be used. At the end of the reaction, the volatiles such as ethyl chloride, diethyl ether, ethanol, and diluent are recovered and recycled. The ethylcellulose in solution is precipitated in the form of granules with further recovery of the carrier solvents. Washing with water completes the processing. Control of metallic impurities is important to achieve stability during storage. Anitoxidants can also be incorporated to inhibit loss of viscosity.

In accordance with the present invention, the EC does not undergo micronization after completion of the synthesis. This form of EC distinguishes itself from the prior art in that it has a higher ethoxyl content (greater than 49.6%) and simultaneously a low viscosity (less than 53 cps) and the average particle size is greater than 50 micrometers.

According to the present invention, ethylcellulose has an ethoxyl content lower limit of 49.6%, preferably 49.8%, and more preferably 50.0%. The upper limit of the ethoxyl content of the EC is 54.88%, preferably 53.0% and more preferably 52.0%. The viscosity of the EC is less than 53.0 cps, preferably less than 25 cps and more preferably less than about 17 cps, with a lower limit of about 3 cps.

Uniquely, it has been found that this high ethoxyl, low viscosity ethylcellulose possesses superior compactibility and compressibility, so resulting in tablets with superior mechanical strength when compared to analogous tablets made of EC with lower ethoxyl content and/or higher viscosity. Furthermore their mechanical strength is also superior to analogous tablets prepared with micronized EC. EC tablets containing 1% stearic acid NF as a lubricant were compressed on a instrumented rotary tablet press (Manesty Beta Press, Thomas Engineering, Hoffman Estates, Ill.) as described under Standard Methods. The mechanical strength was determined by measuring the diametrical crushing strength as described under Standard Methods.

In EC matrix tablets, superior mechanical strength is a key parameter assuring longer release duration. Furthermore increased mechanical strength is a desirable attribute in compressed dosage forms as this assures their physical and dimensional stability and robustness during bulk handling operations such as tablet coating, conveying and filling into final containers and transportation.

A further distinguishing characteristic of the form of EC of this invention is that this material which provides superior compressibility has a lower glass transition temperature (Tg) than analogous materials with poorer compressibility. The preferred form generally has a Tg that is less than 130° C., preferably less than 128° C. (Table 2). The Tg was determined by differential scanning calorimetry (TA Instruments DSC 2920, Newark, Del.) as described under Standard Methods.

Furthermore, this preferred form of EC also has the desirable attribute of good powder flow characteristics and low dustiness. While no single parameter or method to assess powder flow may allow one to completely quantify, describe or predict the flow of a powder, it is accepted industrial practice to jointly consider a number of different parameters which may be indicative of particle-particle interactions and flowability (Banker et al, 1986, ibid). Frequently used parameters include the angle of repose, angle of slide (also known as the internal angle), the compressibility index, as well as determination of the flow rate through the powder through a defined orifice such as that of a glass funnel or tablet press hopper. These are described under the Standard Methods section.

The angle of repose method is generally not predictive for the flow behavior of powders with only small differences in flow (Amidon, G. E., Physical and Mechanical Property Characterization of Powders in "Physcial Characterization of Pharmaceutical Solids", (Brittain, H. G., Ed.), Marcel Dekker Inc., New York, N.Y., 1995, pp. 293–309). However, it is widely accepted that powders with angles of repose equal to or greater than 50° tend to be cohesive powders with poor or no flow through an orifice of a tablet press hopper. Powders with angles of repose close to the practically minimum observable values of 18–25° are generally characterized by good flowability (Marshall, K., Compression and Consolidation of Powdered Solids, in "The Theory and Practice of Industrial Pharmacy," (Lachman, L., Lieberman, H. A. and Kanig, J. L., Eds.), 3$^{rd}$ Edition, Lea and Febiger, Philadelphia, Pa., 1986, p. 67). Further, generally low compressibility values (18%) are frequently correlated with good flow. Generally as this value increases, flow tends to decrease. It should however be noted that exceptions have been documented (Amidon, 1995, ibid). Determining the flow rate of powder through a defined orifice of a funnel is perhaps the simplest test that closely simulates the actual flow conditions to which powders are subjected during tableting.

From Table 1 it is evident that the high ethoxyl, low viscosity EC was characterized as having good flowability as measured by the aforementioned criteria. Conversely, micronized EC demonstrated poor flow.

TABLE 1

Selected Powder Flow Characteristics of EC

| EC Type | Angle of Repose (°) | Angle of Slide (°) | Compressibility Index (%) | Flow Rate (g/sec) |
| --- | --- | --- | --- | --- |
| High ethoxyl (50.8%), low viscosity (9 cps), Aqualon Co. | 24.8 | 35.8 | 12 | 10.99 |

TABLE 1-continued

Selected Powder Flow Characteristics of EC

| EC Type | Angle of Repose (°) | Angle of Slide (°) | Compressibility Index (%) | Flow Rate (g/sec) |
| --- | --- | --- | --- | --- |
| EC NF, micronized, 10 cps, 48.4% ethoxyl, Dow Chemical Co. | 51 | 51.3 | 14 | 0.22* |

*Orifice plugged on every run, flow rate represents average mass after 60 seconds.

PHARMACEUTICALS

According to the present invention, the high ethoxyl, low viscosity EC can be combined with medicaments (or active pharmaceutical ingredients) to prepare a blend suitable for tableting or pelletizing. One or more medicaments may be combined in a single dosage form, depending on the chemical compatibility of the combined active ingredients and the ability to obtain the desired release rate from the dosage form for each active ingredient. The determination of the effective amount of the medicament per dosage unit is easily determined by skilled clinicians.

Representative types of active medicaments include antacids, anti-inflammatory substances, anti-infectives, psychotropics, antimanics, stimulants, antihistamines, laxatives, decongestants, nutritional supplements, gastrointestinal sedatives, antidiarrheal preparations, antianginal drugs, antiarrhythmics, antihypertensive drugs, vasoconstrictors and migraine treatments, anticoagulants and antithrombotic drugs, analgesics, anti-pyretics, hypnotics, sedatives, antiemetics, anti-nauseants, anticonvulsants, neuromuscular drugs, hyper- and hypoglycemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, antiuricemic drugs, topical analgesics, local anesthetics, polypeptide drugs, anti-HIV drugs, chemotherapeutic and anti-neoplastic drugs.

Examples of specific active medicaments include aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol pseudoephedrine, loratadine, theophylline, ascorbic acid, tocopherol, pyridoxine, methoclopramide, magnesium hydroxide, verapamil, procainamide hydrochloride, propranolol, captopril, ergotamine, furazepam, diazepam, lithium carbonate, insulin, furosemide, hydrochlorothiazide, guaiphenesin, dextromethorphan and benzocaine. It should be understood that any active medicament that is physically and chemically compatible with the EC of the present invention and other dosage form ingredients can be used in the present invention.

These active ingredients can be combined and dry blended with the EC to achieve a blend suitable for tableting which is then compressed as described under Standard Methods. Typically such a blend would also include small quantities (less than 5%) of other excipients such as lubricants (e.g., magnesium stearate, stearic acid, calcium stearate, and hydrogenated vegetable oil), antiadherents and flow promoting agents (e.g., talc, colloidal silicon dioxide). Such excipients are necessary for successful high speed, commercial tableting and are well known to those skilled in the art.

Furthermore, a blend may also include other excipients such as fillers, diluents, binders, coloring agents, flavoring agents, and disintegrants. One or more fillers or bulking agents may include dibasic calcium phosphate dihydrate, lactose or starch, with microcrystalline cellulose being the preferred filler. The filler may be present in an amount in the range of from about 0 to about 94 percent of the total weight of the uncoated dosage form, with from about 1 to about 5 weight percent being preferred for high dosage actives and with from about 80 to 85 weight percent being preferred for low dosage actives.

The tablets can be compressed as simple monolithic, cylindrical dosage forms, but are not limited to this simple geometry. Modifications in geometry can include compacts of other shapes as well as compacts having a core that is compression coated with additional barrier coatings. Such a dry compression coat can be applied by means of commercially available compression coating tablet presses such a Drycota® Press (Manesty Co.). The barrier coatings may contain high ethoxyl, low viscosity EC and other excipients as mentioned above, however, it may also contain an active medicament. Alternately, the EC may also be contained in the core.

The processing of these high compression sustained release polymer blends can be done by bag mixing two or more components, by twin shell V-blending, or co-extrusion. Other standard pharmaceutical processing techniques can also be used to form blends with EC. Examples are high-speed roll compaction and direct compaction.

Although the tablet dosage form has been referred to throughout this description, it should be understood that other dosage forms exist, such as multiparticulates in the form of pellets or mini-tablets. If desired, capsules such as hard or soft gelatin capsules can contain the multiparicu-lates. If desired, the multiparticulate oral dosage forms can comprise a blend of at least two populations of pellets or mini-tablets having different controlled-release profiles that are conventional in the sustained release drug industry.

The tablets or pellets of this invention can be coated or uncoated depending on the manufacturer's desires. The coating can be for any purpose such as aesthetics, flavoring, taste masking, or to provide additional controlled release properties.

STANDARD METHODS FOR DETERMINING PROPERTIES

Ethoxyl Content

In accordance with ASTM D4794, Ethoxyl content was determined by a Zeisel (sealed) tube method by reacting EC with hydriodic acid, liberating one mole of ethyl iodide for each mole of ethoxyl substitution on the cellulose chain. The ethyl iodide was then extracted with o-xylene and quanti-tated by gas chromatography using toluene as an internal standard. A typical set of apparatus, reagents and procedures for this test are listed below:

Apparatus

1. Gas chromatograph, Perkin-Elmer 900, or equivalent equipped with thermal conductivity detector, chart recorder, and integrator.
2. Column 6'x⅛" stainless steel packed with 10% SP-2100 on 100/120 Supelcoport, Supelco, Inc., Bellefonte, Pa. Upon receipt, columns were conditioned overnight at 200° C.
3. Reacti-vials, 5 ml, equipped with mininert valves. (Pierce Chemical Co., #13223 and #10135).
4. Silli-Therm Heating Module, 110 v, 19791, Pierce Chemical Co., Rockford, Ill.
5. Reacti-Bar 21 (6) 19785, Pierce Chemical Co., Rockford, Ill.
6. Cover, stainless steel, fabricated to cover six (6) Reacti-Bar 21 units on the Silli-Therm Heating Module
7. Dispenser 0–5 ml, Labindustries Repipet, or equivalent. Syringe, 100 µl, Hamilton 710 N or equivalent.
8. Syringe, Hamilton adjustable set to deliver 1.0 µl injections.
9. Micro-set pipet adjusted to deliver 2.0 ml (Lancer product #8885-890007).
10. Balance: 0.0001 g. readability; 0.0002 g. accuracy.

Reagents

1. Iodoethane, reagent grade (ethyl iodide)
2. Toluene, reagent grade
3. O-xylene, reagent grade
4. Hydriodic acid, 57% solution in water

Gas Chromatograph and Integrator Parameters

| | |
|---|---|
| Oven | 130° C. |
| Injection Port | 200° C. |
| Detector Current | 175 mA |
| Flow Rates: Helium | 30 ml./min. |
| Detector Temperature | 250° C. |
| Attenuation | 3 |
| Chart Speed | 1.0 |
| Peak Width | 0.04 |
| Threshold | 4 |

Integrator parameters are given for Hewlett Packard Reporting Integrator Model 3390A.

Procedure

1. Dried about 0.5 grams of sample in 105° C. oven for 1 hour.
2. Set heating block temperature to 150° C.
3. Into a tared 5 ml reacti-vial, weighed 0.05–0.08 gram of cooled sample. Recorded weight to the nearest 0.0001 gram, samples were run in duplicate or triplicate.
4. Added 2 ml of hydriodic acid using a transfer pipet. Capped sample.
5. Added 2 ml of internal standard solution using the repipet dispenser or equivalent.
6. Immediately recapped vials with mininert valve tops and shook vials. Monitored block temperature at 180+/−5° C. with a thermometer.
7. Placed vials into block and replaced metal cover. Kept samples behind safety shield while heating.
8. Maintained block temperature at 150+/−5° C. for two hours.
9. Removed vials and allowed to cool to room temperature.
10. Shook each sample vigorously and allowed to stand for about 20 minutes.
11. Chromatographed 1.0 µl of the upper solvent layer of each sample on the gas chromatograph.

Viscosity

Viscosity was determined by preparing a 5% solution of EC in a toluene:ethanol (80:20) solvent mixture. Viscosity of the solution was measured using a Hercules Horizontal Capillary Viscometer (following ASTM D914-00, 33.1). The list of apparatus, reagents and procedures are described below.

Apparatus

1. Balance, 0.1 g. accuracy.
2. Buret (optional) capable of delivering 111.8 ml.
3. Bath, constant temperature maintained at 25° C.
4. Eight oz., wide mouth, screw cap bottle with cap.
5. Cellophane or other suitable bottle cap liner.
6. Viscometer, Hercules Horizontal Capillary Viscometer—Calibrated to give viscosity readings in centipoise.
7. Thermometer, marked in 0.1° C. subdivisions.
8. Shaker.

Reagents

1. Ethyl Alcohol, SDA 2B-3 grade.
2. Toluene, meeting ASTM D 362 specification.
3. Toluene:Alcohol solvent, 80:20 by weight.

Procedure

1. Determined the temperature of the 80:20 solvent to be used. The temperature of the solvent must be between 20 and 30° C. if 111.8 ml. burette is to be used in this determination.
2. Weighed 5.0 g. of sample to the nearest 0.1 g.
3. Measured 111.8 ml. of 80:20 solvent from burette (the equivalent of 95.0 grams of solvent) into an 8-oz. bottle. Added the sample to the solvent, making an effort to disperse the sample and avoid lumping. Covered the neck of the bottle with a sheet of cellophane and applied the screw cap.
4. Placed the sample on a shaker and allowed it to shake until dissolution is complete.
5. Placed the bottle into a 25° C. bath for 30 minutes and the solution was free of air bubbles.
6. With the viscometer in the raised position (reservoir vertical), filled the reservoir to the etched mark. Made sure that no air remained trapped in the sample. Placed a finger over the end of the capillary. Released brace and carefully lowered the viscometer to horizontal. (It was essential that the liquid was allowed to come to an equilibrium level before placing the finger over the end of the capillary and lowering it to the horizontal.)
7. Released the finger and measured the time for the liquid to flow from the first to the second mark in the capillary tube. Reported as time t.
8. Calculated the viscosity as follows: N=td/D where:

N=viscosity, cps.

t=time of flow for the sample d=density of sample solution at 25° C. (0.86)

D=density of the oil used for calibration of the viscometer.

Tablet Manufacture

Ethylcellulose tablets were prepared by blending 198 g of EC powder with 2 g of stearic acid NF powder (marketed by Spectrum Chemical, Gardenia, Calif.). The stearic acid powder was hand screened through a 20 mesh hand screen before it was placed in a 1 qt V-blender together with the EC powder. The powders were blended for 3 minutes. The EC and stearic acid blend was compressed on an instrumented Manesty Beta-Press (Thomas Engineering, Hoffman Estates, Ill.) using ⅜ inch flat face beveled edge (FFBE) tooling. Die fill depth was set to achieve 275 mg tablets. The tablets were compressed using 5 kN, 15 kN and 25 kN compression force with the press running at 37.5 rpm.

Drug containing tablets were manufactured by blending the requisite proportion of EC and drug to achieve a batch size of 198 g. The drugs used included phenylpropanolamine USP (marketed by Spectrum Chemical, Gardenia, Calif.), theophylline, anhydrous, USP (marketed by BASF Corp, Mount Olive, N.J.), and acetaminophen USP (marketed by Rhodia Inc, Cranbury, N.J.). The drugs and powders were passed through a 20-mesh screen by hand before placing them together in a 1 qt V-blender. The powders were then mixed for 15 minutes. Thereafter, 2 g of stearic acid was blended into the mixture that was then tableted as described above. Additional batches of the drugs and EC were blended together with additional amounts of microcrystalline cellulose to form the tablets.

Mechanical Strength

A Schleuniger Model 6d hardness tester (Vector Corp.) was used to measure the diametrical crushing force in order to assess the mechanical strength of the tablets. The results were reported in kP (kilopond) units for an average of 10 tablets. A modified compression procedure was used for micronized EC (to be described in Example 2).

Glass Transition Temperature (Tg)

The Tg was determined from a differential scanning calorimetry thermogram. Differential scanning calorimetry was performed using a TA Instruments (Newark, Del.) DSC 2920 standard cell attached to a Refrigerated Cooling Accessory. To obtain accurate results, the DSC 2920 was calibrated using the same heating rate and purge conditions used for the samples. Calibration included heating the empty cell through the temperature range of interest to perform the baseline slope and offset calibration. And secondly, heating a certified Indium Standard (99.99% pure) through the melting point to obtain both the DSC cell constant and the onset slope values. To prepare a sample, approximately 10.0 milligrams of ethylcellulose (accurately weighed) was encapsulated into a TA Instruments crimped aluminum robot pan with lid. The sample was then loaded into the DSC 2920 cell, cooled 5° C./minute from room temperature to −20° C., then heated at 5.0° C./minute under a zero grade nitrogen purge from −20° C. to 280° C. The heat flow and temperature data, from the heating cycle, were recorded. The heat data were analyzed using TA Universal Analysis 2000 software. The glass transition measurement reported the onset temperature, the half-height temperature (half height defines the midpoint as the Y-axis value halfway between the onset and end of the step/glass transition region) and the transition ending temperature.

Angle of Repose

A standard laboratory glass funnel with smooth surfaces and an orifice whose inner diameter is 9 mm was affixed two inches above a stainless steel platform. While keeping the orifice blocked, 10.0 g of powder was loaded into the funnel. By unblocking the orifice, the powder was allowed to flow onto the platform under the force of gravity and, when necessary, with the use of light tapping. The angle of repose was then determined by measuring the apex angle with a protractor (Starrett, Model C 183) and performing the following calculation:

$$\text{Angle of repose} = (180° - \text{apex angle})/2$$

In addition, photographs were taken of the powder cone, to further validate the angle measurements.

Angle of Slide

The angle of slide was determined by placing 1 g of powder in a 1-inch square stainless steel frame (0.5 inch high), which was resting on a stainless steel platform. The frame was then removed leaving behind an approximately square shaped heap of powder on the platform. One end of the platform was then incrementally raised until the entire powder sample slid off the platform. The angle of slide was then calculated from the height of lift and the length of the platform:

Angle of slide=sin$^{-1}$(height of lift, length)

Compressibility Index

To determine the compressibility index, the aerated and tapped bulk densities were first measured. Aerated bulk density was determined as follows. The test material in powder form was slowly added up to the 100-ml marking of a pretared, graduated 100-ml cylinder. Care was taken so as not to disturb the powder bed during addition. The weight of the added material was then recorded. Bulk density was then calculated from the weight and volume of the material.

Tapped bulk density was then determined as follows. The filled graduated cylinder from the bulk density determination was placed on a Vanderkamp Tap Density Tester. The apparatus was set for 100 taps. At the end of the test, the volume of the powder in the cylinder was recorded. The tap density was then calculated dividing the bulk density weight by the powder volume.

The compressibility index was then calculated as follows:

$$\text{Compressibility} \% = 100 \times \frac{(\text{Tapped bulk density} - \text{Aerated bulk density})}{\text{Tapped bulk density}}$$

Mass Flow Rate Through a Defined Orifice

The flow rate was measured by affixing a standard laboratory glass funnel with an orifice of 9.37 mm inner diameter at a distance of 100 mm above the weighing platform of an analytical balance (Mettler Toledo, Columbus, Ohio). While blocking the orifice, 18.0 g of powder was loaded into the funnel. The orifice was then unblocked and the powder was allowed to flow under force of gravity into a pretared glass beaker located on the weighing platform. The elapsed time between unblocking the orifice and the cessation of powder flow was recorded with the aid of a digital stopwatch. Five sets of mass and time measurements were then used to calculate the average flow rates.

EXAMPLE 1

Ethylcellulose materials (marketed by Aqualon, Division of Hercules Incorporated, Wilmington, Del.) with varying viscosities and ethoxyl percentages were blended with 1% stearic acid as a lubricant and compressed on an instrumented rotary tablet press as previously described in the Standard Method section. The results presented are for 275 mg tablets compressed at a constant force of 25 kN, while operating at a press speed of about 37.5 rpm. As can be seen in Table 2, the three EC samples with an ethoxyl content with a lower limit of 49.65% and a viscosity less than 50 cps yield tablets with clearly superior crushing strength. These are further identified by the clearly lower Tg values of 124.6° C. and 124.2° C., respectively.

TABLE 2

Effect variation in viscosity and ethoxyl % on crushing strength of compressed EC tablets

| % Ethoxyl | Viscosity (cps) | Crushing Strength (kP) | Tg (° C.) |
| --- | --- | --- | --- |
| 45.6 | 7.1 | 11.3 | 134.5 |
| 46.3 | 83.5 | 10.2 | 136.5 |
| 47.5 | 90.0 | 14.2 | 134.2 |
| 49.3 | 33.5 | 13.1 | 130.8 |
| 49.3 | 80.0 | 15.4 | 132.7 |
| 50.8 | 9.0 | 18.8 | 124.6 |
| 51.0 | 9.2 | 18.8 | 124.2 |
| 50.0 | 24 | 18.3 | 127.6 |
| 49.6 | 94.0 | 16.1 | 129.5 |
| 50.7 | 98.0 | 16.9 | 131.8 |
| 49.8 | 136.0 | 13.2 | 134.0 |

Example 2

High ethoxyl (50.8%), low viscosity (9 cps) EC powder (marketed by Aqualon, Division of Hercules Incorporated, Wilmington, Del.) was compared with commercially available pharmaceutical grade micronized EC NF powder (Ethocel® Premium products, Standard 10 FP, marketed by The Dow Chemical Co., Midland, Mich.) having 48.4% ethoxyl and 10.2 cps viscosity and average particle size of less than or equal to 15 micrometers. The powders were lubricated with 1% stearic acid NF (marketed by Spectrum, Gardenia, Calif.) in a V-blender and were then compressed on the previously described instrumented rotary press fitted with a single set of compression tooling. Due to the inability of the micronized EC to flow from the tablet hopper, the die cavity was filled manually with 180 mg of lubricated EC powder. The powder to be filled was accurately weighed on an analytical balance. Due to the low bulk density of micronized EC powder only 180 mg could be accommodated in the die cavity. This mass was, therefore, also used for comparison purposes with high ethoxyl, low viscosity EC. The results are shown in Table 3 below.

TABLE 3

Diametrical Crushing Force vs. Compaction Force for high ethoxyl, low viscosity EC and commercially available pharmaceutical grade micronized EC.

| Ethylcellulose Type | Compression Force (kN) | Crushing Force (kP) |
| --- | --- | --- |
| High Ethoxyl, Low Viscosity EC | 4.7 | 12.0 |
|  | 14.0 | 16.3 |
|  | 22.0 | 17.3 |
| Micronized EC, NF | 5.3 | 9.8 |
|  | 15.3 | 12.1 |

Example 3

High ethoxyl (50.8%), low viscosity (9 cps) EC powder was blended in a 3:1 ratio with acetominophen USP powder (marketed by Spectrum Chemical Co., Gardenia, Calif.) in a 1 qt V-blender for 15 minutes. 2 g of stearic acid were then added to 198 g of the blend by handscreening through a 20 mesh screen. The mixture was further blended for 3 minutes and was then compressed at constant pressure (25 kN compaction force) and speed (37.5 rpm) on an instrumented rotary tablet press as previously described under Standard Methods. For reference, additional batches were prepared which contained EC with lower ethoxyl content than 49.6% and/or higher viscosity than 10 cps. The results clearly show that the high ethoxyl, low viscosity EC containing tablets have a superior crushing strength (Table 4).

TABLE 4

Crushing strength of acetaminophen
tablets containing different types of EC

| % Ethoxyl | Viscosity (cps) | Crushing Strength (kP) |
| --- | --- | --- |
| 50.8 | 7.2 | 14.0 |
| 49.6 | 94.0 | 9.6 |
| 45.6 | 7.1 | 7.7 |
| 46.3 | 83.5 | 4.7 |

Example 4

High ethoxyl (50.8%), low viscosity (9 cps) EC powder was blended in a 1:1 ratio with acetominophen USP powder in a 1 qt V-blender for 15 minutes. 2 g of stearic acid were then added to 198 g of the blend by handscreening through a 20-mesh screen. The mixture was further blended for 3 minutes and was then compressed at constant pressure (25 kN compaction force) and speed (37.5 rpm) on an instrumented rotary tablet press as previously described under Standard Methods. The crushing strength of the tablets was 9.8 kP. The analogous powder blend containing micronized EC NF powder could not be compressed into tablets because of inadequate powder flow.

Example 5

High ethoxyl (50.8%), low viscosity (9 cps) EC powder was blended with acetominophen USP powder and microcrystalline cellulose(Avicel(® PH102, FMC Corporation, Philadelphia, Pa.) in a 1 qt V-blender for 15 minutes. The relative proportions were EC: acetaminophen: microcrystalline cellulose (40:25:35). 2 g of stearic acid was then added to 198 g of the blend by hand screening through a 20-mesh screen. The mixture was further blended for 3 minutes and was then compressed at constant pressure (25 kN compaction force) and speed (37.5 rpm) on an instrumented rotary tablet press as previously described under Standard Methods. The crushing strength of the tablets was 15.0 kP.

Example 6

High ethoxyl (50.8%), low viscosity (9 cps) EC powder was blended in a 3:1 ratio with theophylline USP powder (marketed by BASF Corporation, Mount Olive, N.J.) in a 1 qt V-blender for 15 minutes. 2 g of stearic acid were then added to 198 g of the blend by hand screening through a 20-mesh screen. The mixture was further blended for 3 minutes and was then compressed at constant pressure (25 kN compaction force) and speed (37.5 rpm) on an instrumented rotary tablet press as previously described under Standard Methods. For comparison purposes, additional batches were prepared that contained EC with lower ethoxyl content than 49.6% and/or higher viscosity than 10 cps. The results reported in Table 5 clearly show that the high ethoxyl, low viscosity EC containing tablets have a superior crushing strength.

TABLE 5

Crushing Strength of theophylline
tablets containing different types of EC

| % Ethoxyl | Viscosity (cps) | Crushing Strength (kP) |
| --- | --- | --- |
| 50.8 | 7.2 | 15.7 |
| 49.6 | 94.0 | 12.3 |
| 45.6 | 7.1 | 10.4 |
| 46.3 | 83.5 | 8.6 |

Example 7

High ethoxyl (50.8%), low viscosity (9 cps) EC powder was blended in a 3:1 ratio with phenylpropanolamine USP powder (marketed by Spectrum Chemical Co., Gardenia, Calif.) in a 1 qt V-blender for 15 minutes. 2 g of stearic acid were then added to 198 g of the blend by hand screening through a 20-mesh screen. The mixture was further blended for 3 minutes and was then compressed at constant pressure (25 kN compaction force) and speed (37.5 rpm) on an instrumented rotary tablet press as previously described under Standard Methods. For comparison, additional batches were prepared that contained EC with lower ethoxyl content than 49.6% and/or higher viscosity than 10 cps. The results clearly show that the high ethoxyl, low viscosity EC containing tablets have a superior crushing strength (Table 6).

TABLE 6

Crushing Strength of phenylpropanolamine
tablets containing different types of EC.

| % Ethoxyl | Viscosity (cps) | Crushing Strength (kP) |
| --- | --- | --- |
| 50.8 | 7.2 | 11.0 |
| 45.6 | 7.1 | 6.0 |
| 46.3 | 83.5 | 4.0 |

While this invention has been described with respect to specific embodiments, it should be understood that these embodiments are not intended to be limiting and that many variations and modifications can be made without departing from the spirit and scope of the invention; therefore, only such limitations should be imposed as are indicated by the appended claims.

What is claimed:

1. A pharmaceutical dosage form composition comprising
    a) ethylcellulose that has an ethoxyl range lower limit of 49.6%, a viscosity of less than 53 cps as measured on a Hercules Horizontal Capillary Viscometer at a temperature of 25° C. in a 5% solution, and a glass transition temperature (Tg) of less than 130° C., and
    b) at least one active pharmaceutical ingredient, wherein the dosage form is a tablet or pellet and has a compression strength greater than an analogous dosage form comprising ethylcellulose of similar form but has an ethoxyl range less than 49.6%.

2. The pharmaceutical dosage form composition of claim 1, wherein the ethylcellulose has a glass transition temperature (Tg) of less than 128° C.

3. The pharmaceutical dosage form composition of claim 1, wherein the ethylcellulose has an average particle size of greater than 50 micrometers.

4. The pharmaceutical dosage form composition of claim 1, wherein the pharmaceutical dosage form has a compression strength greater than an analogous dosage form comprising ethylcellulose of similar form but has a viscosity of greater than 50 cps.

5. The pharmaceutical dosage form composition of claim 1, wherein the dosage form is a multiparticulate.

6. The pharmaceutical dosage form composition of claim 1, wherein ethylcellulose is in a barrier coating.

7. The pharmaceutical dosage form composition of claim 1, wherein the lower limit of the ethoxyl range is 49.8%.

8. The pharmaceutical dosage form composition of claim 1, wherein the lower limit of the ethoxyl range is 50.0%.

9. The pharmaceutical dosage form composition of claim 1, wherein the upper limit of the ethoxyl range is 54.88%.

10. The pharmaceutical dosage form composition of claim 1, wherein the upper limit of the ethoxyl range is 53.0%.

11. The pharmaceutical dosage form composition of claim 1, wherein the upper limit of the ethoxyl range is 52.0%.

12. The pharmaceutical dosage form composition of claim 1, wherein the upper limit of the ethylcellulose viscosity is less than 25 cps.

13. The pharmaceutical dosage form composition of claim 1, wherein the upper limit of the ethylcellulose viscosity is less than 17 cps.

14. The pharmaceutical dosage form composition of claim 1, wherein the lower limit of the ethylcellulose viscosity is about 3 cps.

15. The pharmaceutical dosage form composition to claim 1 wherein the active pharmaceutical ingredient is selected from the group consisting of antacids, anti-inflammatory substances, anti-infectives, psychotropics, antimanics, stimulants, antihistamines, laxatives, decongestants, nutritional supplements, gastrointestinal sedatives, antidiarrheal preparations, antianginal drugs, antiarrhythmics, antihypertensive drugs, vasoconstrictors and migraine treatments, anticoagulants and anti-thrombotic drugs, analgesics, antipyretics, hypnotics, sedatives, antiemetics, anti-nauseants, anticonvulsants, neuromuscular drugs, hyper- and hypoglycemic agents, thyroid and antithyroid preparations, diuretics, antispasmodics, uterine relaxants, mineral and nutritional additives, anti-obesity drugs, anabolic drugs, erythropoietic drugs, antiasthmatics, expectorants, cough suppressants, mucolytics, antiuricemic drugs, topical analgesics, local anesthetics, polypeptide drugs, anti-HIV drugs, chemotherapeutic and anti-neoplastic drugs and mixtures thereof.

16. The pharmaceutical dosage form composition of claim 6 wherein the active pharmaceutical ingredients are selected from the group consisting of phenylpropanolamine hydrochloride, aluminum hydroxide, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephedrine, loratadine, theophylline, ascorbic acid, tocopherol, pyridoxine, methoclopramide, magnesium hydroxide, verapamil, procainamide hydrochloride, propranolol, captopril, ergotamine, flurazepam, diazepam, lithium carbonate, insulin, furosemide, hydrochlorothiazide, guaiphenesin, dextromethorphan, benzocaine, and mixtures thereof.

17. The pharmaceutical dosage form of claim 1, wherein the ethylcellulose has high flowability as measured by an angle of repose of less than 35°, or an angle of slide of less than 45°.

* * * * *